United States Patent [19]

Andrews

[11] Patent Number: 5,457,131
[45] Date of Patent: Oct. 10, 1995

[54] CYCLOPENTANE(ENE) HEPTANOIC OR CYCLOPENTANE(ENE) HEPTENOIC ACID, 2-HYDROCARBYL SULFONAMIDOMETHYL AND DERIVATIVES THEREOF AS THERAPEUTIC AGENTS

[75] Inventor: Steven W. Andrews, Irvine, Calif.

[73] Assignee: Allergan, Inc., Irvine, Calif.

[21] Appl. No.: 292,543

[22] Filed: Aug. 18, 1994

Related U.S. Application Data

[62] Division of Ser. No. 108,209, Aug. 17, 1993, Pat. No. 5,387,608.

[51] Int. Cl.$^6$ .................. A61K 31/215; A61K 31/195; C07C 69/74; C07C 405/00
[52] U.S. Cl. .................. 514/604; 514/183; 514/357; 514/438; 514/459; 514/471; 514/523; 514/530; 514/601; 514/605; 546/338; 549/75; 549/421; 549/491; 552/10; 558/408; 560/12; 560/121; 560/122; 562/430; 562/503; 564/80; 564/90; 564/92; 564/93; 564/94
[58] Field of Search .................. 560/12, 121, 122; 562/430, 503; 564/80, 92, 94, 90, 93; 514/530, 562, 913, 183, 357, 438, 459, 471, 523, 601, 604, 605; 546/338; 549/75, 421, 491; 552/10; 558/408

[56] References Cited

U.S. PATENT DOCUMENTS

| | | | |
|---|---|---|---|
| 4,599,353 | 7/1986 | Bito | 514/530 |
| 4,994,274 | 2/1991 | Chan et al. | 424/427 |
| 5,001,153 | 3/1991 | Ueno et al. | |
| 5,034,413 | 7/1991 | Chan et al. | 514/530 |

FOREIGN PATENT DOCUMENTS

| | | |
|---|---|---|
| 0364417 | 4/1990 | European Pat. Off. |
| 4037941 | 5/1992 | Germany |

OTHER PUBLICATIONS

Bito, L. Z., "Prostaglandins and Related Compounds as Potential Ocular Therapeutic Agents," *Biological Protection with Prostaglandins*, Cohen, M. M., ed., Boca Raton, Fla., CRC Press, Inc., 1985, pp. 231–252.

Bito, L. Z., "Prostaglandins, Other Eicosanoids, and Their Derivatives as Potential Antiglaucoma Agents," *Applied Pharmacology in the Medical Treatment of Glaucomas* Drance, S. M. and Neufeld, A. H. eds., New York, Grune & Stratton, 1984, pp. 477–505.

Nilsson, et. al., "PGF$_{2\alpha}$ Increases Uveoscleral Outflow," *Invest. Ophthalmol. Vis. Sci.* (suppl), 284, 1987.

Siebold, et. al., "Esterified prostaglandin shows 'potent' promise," *Prodrug* 5 3, 1989.

Bito, L. Z., "Prostaglandins, Old Concepts and New Perspectives," *Arch. Ophthalmol.* 105, 1036, 1987.

*Primary Examiner*—Peter O'Sullivan
*Attorney, Agent, or Firm*—Robert J. Baran; Martin A. Voet; Howard R. Lambert

[57] ABSTRACT

The present invention relates to cyclopentane heptanoic or cyclopentane heptenoic acid, 2-hydrocarbyl sulfonamidomethyl, and derivatives thereof, useful as therapeutic agents. In particular, the therapeutic agents of this invention are useful as ocular hypotensives.

30 Claims, 2 Drawing Sheets

FIG. 1.

_FIG. 2._

_FIG. 3._

CYCLOPENTANE(ENE) HEPTANOIC OR CYCLOPENTANE(ENE) HEPTENOIC ACID, 2-HYDROCARBYL SULFONAMIDOMETHYL AND DERIVATIVES THEREOF AS THERAPEUTIC AGENTS

This is a divisional of application Ser. No. 08/108,209, filed on Aug. 17, 1993, now U.S. Pat. No. 5,387,608.

FIELD OF THE INVENTION

The present invention relates to cyclopentane (or cyclopentene) heptanoic or eyelopentane (or cyclopentene) heptenoic acid, 2-hydrocarbyl sulfonamidomethyl, esters and other derivatives thereof, which may be substituted in the 3 and/or 5-position of the cyclopentane or cyclopentene ring with hydroxyl or oxo groups, e.g., cyclopentane heptenoic acid, 2-phenylethylsulfonamidomethyl, 3,5-dihydroxy and alkyl esters thereof. The compounds of the present invention are potent ocular hypotensives, and are particularly suitable for the management of glaucoma. Moreover, the compounds of this invention are smooth muscle relaxants with broad application in systemic hypertensive and pulmonary diseases; smooth muscle relaxants with application in gastrointestinal disease, reproduction, fertility, incontinence, shock, etc.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr, M.S. *Exp, Eye Res.* 1971, 11, pp. 170–177; Bito, L. Z. *Biological Protection with Prostaglandins* Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505). Such prostaglandins include $PGF_{2\alpha}$, $PGF_{1\alpha}$, $PGE_2$, and certain lipid-soluble esters, such as $C_1$ to $C_5$ alkyl esters, e.g. 1-isopropyl ester, of such compounds.

In the U.S. Pat. No. 4,599,353 certain prostaglandins, in particular $PGE_2$ and $PGF_{2\alpha}$ and the $C_1$ to $C_5$ alkyl esters of the latter compound, were reported to possess ocular hypotensive activity and were recommended for use in glaucoma management.

Although the precise mechanism is not yet known, recent experimental results indicate that the prostaglandin-induced reduction in intraocular pressure results from increased uveoscleral outflow [Nilsson et al., *Invest, Ophthalmol. Vis. Sci.* 28(suppl), 284 ( 1987)].

The isopropyl ester of $PGF_{2\alpha}$ has been shown to have significantly greater hypotensive potency than the parent compound, which was attributed to its more effective penetration through the cornea. In 1987 this compound was described as "the most potent ocular hypotensive agent ever reported." [See, for example, Bito, L. Z., *Arch. Ophthalmol,* 105, 1036 (1987), and Siebold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potential of prostaglandins in the management of conditions associated with increased ocular pressure, e.g. glaucoma, is greatly limited by these side effects.

Certain phenyl and phenoxy mono, tri and tetra nor prostaglandins and their 1-esters are disclosed in European Patent Application 0,364,417 as useful in the treatment of glaucoma or ocular hypertension.

In a series of co-pending United States patent applications assigned to Allergan, Inc. prostaglandin esters with increased ocular hypotensive activity accompanied with no or substantially reduced side-effects are disclosed. The co-pending U.S. Ser. No. 386,835 (filed 27 Jul. 1989), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 357,394 (filed 25 May 1989). Similarly, 11,15- 9,15- and 9,11-diesters of prostaglandins, for example 11,15-dipivaloyl $PGF_{2\alpha}$ are known to have ocular hypotensive activity. See the pending patent applications U.S. Ser. No. 385,645 filed 27 Jul. 1990, now U.S. Pat. No. 4,494,274; 584,370 which is a continuation of U.S. Ser. No. 386,312, and 585,284, now U.S. Pat. No. 5,034,413 which is a continuation of U.S. Ser. No. 386,834, where the parent applications were filed on 27 Jul. 1989. The disclosures of these patent applications are hereby expressly incorporated by

SUMMARY OF THE INVENTION

We have found that certain cyclopentane(ene) heptanoic or cyclopentane(ene) heptenoic acid, 2-hydrocarbylsulfonamidomethyl compounds and derivatives thereof have pronounced effects on smooth muscle and are potent ocular hypotensive agents. We have further found that when utilized as ocular hypotensive agents such compounds surprisingly, cause no or significantly low ocular surface hyperemia.

The present invention relates to methods of treating cardiovascular, pulmonary-respiratory, gastrointestinal, reproductive, allergic disease, shock and ocular hypertension which comprises administering an effective amount of a cyclopentane(ene) heptanoic or cyclopentane(ene) heptenoic acid, 2-hydrocarbyl sulfonamidomethyl compound or derivative thereof represented by the formula I wherein the dashed bonds represent a single bond or a double bond which can be in the cis or trans configuration; A is a radical selected from the group consisting of halo, hydrogen, hydroxyl, nitro, amino, cyano, azido, oxime, thiol, alkoxy and thioether radicals; Z is oxo or represents two hydrogen radicals, provided that Z represents two hydrogen radicals when A is halo, hydrogen, azido, cyano or nitro; B is an alkyl or an alkylcycloalkyl radical having from one to ten carbon atoms, e.g. about six to eight carbon atoms, or an arylalkyl radical, selected from the group consisting of hydrocarbyl arylalkyl and heteroarylalkyl radicals wherein the heteroatom is selected from the group consisting of nitrogen, oxygen and sulfur atoms and said arylalkyl radical may comprise up to twelve carbon atoms; $R_3$ is hydrogen or a lower alkyl radical having from 1 to 3 carbon atoms; and $R_1$ and $R_2$ are as defined below. For example, B may be selected from the group consisting of methyl, ethyl, propyl, butyl, cyclopentylethyl, cyclohexylethyl, phenylethyl, thienylethyl, furanylethyl, pyridylethyl, etc. Moreover, B may be substituted by radicals represented by X, as defined below.

More preferably the method of the present invention comprises administering a cyclopentane(ene) heptanoic or cyclopentane(ene) heptenoic acid, 2-(phenyl alkylsulfonamidomethyl) compound represented by the formula II wherein y is 0, or an integer of from 1 to 4, e.g. 1, 2 or 3; X is a radical selected from the group consisting of halo, e.g. fluoro, chloro, etc., nitro, amino, thiol, hydroxy, alkyloxy, alkylcarboxy radicals, etc. and the symbols $R_1$ and $R_2$ are as defined below.

Preferably the compound used in the above method of treatment is a compound of formula (III).

wherein hatched lines indicate α configuration, solid triangles are used to indicate β configuration; one of $R_1$ and $R_2$ is =O, —OH or a —O(CO)$R_6$ group, and the other one is —OH or —O(CO)$R_6$, or $R_1$ is =O and $R_2$ is H; wherein $R_6$ is a saturated or unsaturated acyclic hydrocarbon group having from 1 to about 20 carbon atoms, or —(CH$_2$)$_m$R$_7$ wherein m is 0–10, and $R_7$ is an aliphatic ring from about 3 to about 7 carbon atoms, or an aryl or heteroaryl ring, as defined above; or a pharmaceutically acceptable salt thereof. Preferably $R_1$ and $R_2$ are —OH.

In another aspect, the present invention relates to a method of treating cardiovascular, pulmonary-respiratory, gastrointestinal, reproductive and allergic diseases, shock and ocular hypertension which comprises administering to a subject a pharmaceutical composition comprising a therapeutically effective amount of a cyclopentane heptenoic acid or derivative thereof of formula (IV)

wherein the symbols and substituents are as defined above, in combination with a pharmaceutical carrier.

In a further aspect, the present invention relates to pharmaceutical compositions comprising a therapeutically effective amount of a compound of formulae (I), (II), (III), or (IV) wherein the symbols have the above meanings, or a pharmaceutically acceptable salt thereof in admixture with a non-toxic, pharmaceutically acceptable liquid vehicle.

In a still further aspect, the present invention relates to cyclopentane heptenoic acid, 5-cis-2-(phenylethylsulfonamidomethyl), esters and other derivatives thereof, of the above formulae, wherein the substituents and symbols are as defined hereinabove, or a pharmaceutically acceptable salt of such compounds.

DETAILED DESCRIPTION OF THE INVENTION

The present invention relates to the use of cyclopentane(ene) heptanoic or cyclopentane(ene) heptenoic acid, 2-hydrocarbyl sulfonamidomethyl compounds and derivatives thereof as therapeutic agents, e.g. as ocular hypotensives. These therapeutic agents are represented by compounds having the formula I, as defined above.

The preferred cyclopentane(ene) heptanoic or cyclopentane(ene) heptenoic acid, 2-(phenylalkylsulfonamidomethyl) compounds and derivatives thereof used in accordance with the present invention are encompassed by the following structural formula (II)

wherein the substituents and symbols are as hereinabove defined.

More preferably the therapeutic agents of the present invention are represented by formula (III).

wherein the substituents and symbols are as defined above.

More preferably, the therapeutic agents utilized in the present invention are compounds represented by the formula (IV)

wherein the substituents and the symbols are as defined above.

Most preferably the present invention utilizes the novel compounds of the formula (V)

In all of the above formulae, as well as in those provided hereinafter, the lines represent bonds. Where there is no symbol for the atoms between the bonds, the appropriate carbon-containing radical is to be inferred. For example in formula V, the radical between the phenyl ring and the sulfoxy radical is a methylene ($CH_2$) radical. The radical adjacent the double bond is a CH radical. Moreover, the dotted lines on bonds indicate a single or a double bond which can be in the cis or trans configuration. If two solid lines are used that indicates a specific configuration for that double bond. Hatched lines indicate the α configuration. If one were to draw the β configuration, a solid triangular line would be used.

In the compounds used in accordance with the present invention, compounds having substituents in the α or β configuration are contemplated. As hereinabove mentioned, in all formulas provided herein broken line or hatched attachments to the cyclopentane ring indicate substituents in the a configuration. Thickened solid line or triangle attachments to the cyclopentane ring indicate substituents in the β configuration.

For the purpose of this invention, unless further limited, the term "alkyl" refers to alkyl groups having from one to ten carbon atoms, the term "cycloalkyl" refers to cycloalkyl groups having from three to seven carbon atoms, the term "aryl" refers to aryl groups having from four to ten carbon atoms. The term "saturated or unsaturated acyclic hydrocarbon group" is used to refer to straight or branched chain, saturated or unsaturated hydrocarbon groups having from one to about 6, preferably one to about 4 carbon atoms. Such groups include alkyl, alkenyl and alkynyl groups of appropriate lengths, and preferably are alkyl, e.g. methyl, ethyl, propyl, butyl, pentyl, or hexyl, or an isomeric form thereof. The term "hydrocarbyl" refers to radicals comprising hydrogen and carbon atoms and may have up to 20 carbon atoms. In the "heteroatom-substituted hydrocarbon" the heteroatom-carbon bond replaces either a carbon-hydrogen or a carbon-carbon bond of the above hydrocarbyl radical.

The definition of $R_6$ may include a cyclic component, —$(CH_2)_m R_7$, wherein n is 0–10, $R_7$ is an aliphatic ring from about 3 to about 7 carbon atoms, or an aromatic or heteroaromatic ring. The "aliphatic ring" may be saturated or unsaturated, and preferably is a saturated ring having 3–7 carbon atoms, inclusive. As an aromatic ring, R7 preferably is phenyl, and the heteroaromatic rings have oxygen, nitrogen or sulfur as a heteroatom, i.e., $R_7$ may be thienyl, furanyl, pyridyl, etc. Preferably m is 0–4.

A is preferably selected from the group consisting of:

—$NO_2$, —OH, —$N(R_4)(R_4)$, —SH, —$SH_5$ and —$OR_5$ wherein $R_4$ is hydrogen or $C_1$ to $C_3$ alkyl, and $R_5$ is $C_1$ to $C_3$ alkyl. Preferably $R_4$ is hydrogen.

Preferred representatives of the compounds within the scope of the present invention are the compounds of formula V i.e. cyclopentane heptenoic acid or $C_1$ to $C_3$ alkyl esters thereof, or cyclopentane heptanol, 5-cis, 2-(phenylethylsulfonamidomethyl) -3, 5-dihydroxy, [$1_\alpha$, $2_\beta$, $3_\alpha$, $5_\alpha$] and the 9- and/or 11-esters of these compounds. (The numbered designations in brackets refer to the positions on the cyclopentane ring.)

The following novel compounds may be used in the pharmaceutical compositions and the methods of treatment of the present invention.

(1) cyclopentane heptenoic acid-5-cis-2-(phenylethylsulfonamidomethyl )- 3, 5 dihydroxy, [$1_{6\beta}$, $2_\beta$, $3_\alpha$, $5_\alpha$]

(2) cyclopentane heptenoic acid-5-cis-2-(phenylethylsulfonamidomethyl)- 3, 5 dihydroxy, methylester, [$1_\alpha$, $2_\beta$, $3_\alpha$, $5_\alpha$]

(3) cyclopentane heptenol-5-cis-2-(phenylethylsulfonamidomethyl)- 3, 5 dihydroxy, [$1_\alpha$, $2_\beta$, $3_\alpha$, $5_\alpha$]

(4) cyclopentane heptenamide-5-cis-2-(phenylethylsulfonamidomethyl)- 3, 5 dihydroxy, [$1_\alpha$, $2_\beta$, $3_\alpha$, $5_\alpha$]

(5) cyclopentane N,N-dimethylheptenamide-5-cis-2(phenylethylsulfonamidomethyl)- 3, 5 dihydroxy, [$1_\alpha$, $2_\beta$, $3_\alpha$, $5_\alpha$]

(6) cyclopentane heptenyl methoxide-5-cis-2-(phenylethylsulfonamidomethyl)- 3, 5 dihydroxy, [$1_\alpha$, $2_\beta$, $3_\alpha$, $5_\alpha$]

(7) cyclopentane heptenyl fluoride-5-cis-2-(phenylethylsulfonamidomethyl)- 3, 5 dihydroxy, [$1_\alpha$, $2_\beta$, $3_\alpha$, $5_\alpha$]

(8) cyclopentane heptenyl nitrate-5-cis-2-(phenylethylsulfonamidomethyl)- 3, 5 dihydroxy, [$1_\alpha$, $2_\beta$, $3_\alpha$, $5_\alpha$]

(9) cyclopentane heptenyliodide-5-cis-2-(phenylethylsulfonamidomethyl)- 3, 5 dihydroxy, [$1_\alpha$, $2_\beta$, $3_\alpha$, $5_\alpha$]

(10) cyclopentane hepteneamine-5-cis-2-(phenylethylsulfonamidomethyl)- 3, 5 dihydroxy, [$1_\alpha$, $2_\beta$, $3_\alpha$, $5_\alpha$] phenylethylsul-fonamidomethyl (11) cyclopentane heptene-5-cis-2-(phenylethylsulfonamidomethyl)- 3, 5 dihydroxy, [$1_\alpha$, $2_\delta$, $3_\alpha$, $5_\alpha$]

(12) cyclopentane N-isopropyl heptene amide-5-cis-2-(phenylethylsulfonamidomethyl)- 3, 5 dihydroxy, [$1_\alpha$, $2_\beta$, $3_\alpha$, $5_\alpha$]

(13) cyclopentane N-ethyl heptene amide-5-cis-2-(phenylethylsulfonamidomethyl)- 3, 5 dihydroxy, [$1_\alpha$, $2_\beta$, $3_\alpha$, $5_\alpha$]

(14) cyclopentane N-methyl heptene amide-5-cis-2-(phenylethylsulfonamidomethyl)- 3, 5 dihydroxy, [$1_\alpha$, $2_\beta$, $3_\alpha$, $5_\alpha$]

A pharmaceutically acceptable salt is any salt which retains the activity of the parent compound and does not impart any deleterious or undesirable effect on the subject to whom it is administered and in the context in which it is administered. Such salts are those formed with pharmaceutically acceptable cations, e.g., alkali metals, alkali earth metals, etc.

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred Chelating agent is edentate disodium, although other chelating agents may also be used in place of or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 0–10 |
| buffer | 0.01–10 |
| pH adjustor | q.s. pH 4.5–7.5 |
| antioxidant | as needed |
| surfactant | as needed |
| purfied water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, nontoxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop usually is about 20–35 μl.

The invention is further illustrated by the following non-limiting Examples wherein the compounds are numbered in accordance with the numbered steps of the reaction schemes set forth in the Drawing Figures.

EXAMPLE 1

3-Hydroxy-6β-t-butyldimethylsilyloxymethyl -7α-tetrahydropyranyloxy - 2-oxabicyclo[3.3.0]octane (2).

To a solution of the 3-oxo-6β-t-butlydimethylsilyloxymethyl(OTBDMS)- 7α-tetrahydropyranyloxy(THPO)-2-oxabicyclo[ 3.3.0]-octane, (1), (11.1 g, 29.9 mmol) in anhydrous dichloromethane (150 mL) at −78° C. was added dropwise a 1.0 M stock solution of diisobutylaluminum hydride (diBAL) in dichloromethane (45 mL, 45 mmol). The reaction was maintained at −78 ° C. for 1.5 h, then was quenched by canula into a rapidly stirring mixture of water (4.2 mL, 230 mmol) in dichloromethane (150 mL) over 20 min. The resulting turbid white mixture was vigorously stirred at room temperature for 70 min, then was filtered through a plug of celite to remove the aluminum salts. Concentration under vacuum yielded 2 (9.50 g, 25.5 mmol, 85%) as a clear, slightly yellow oil. This material was used without further purification. $R_f$=0.36 in ethyl acetate-hexanes, 1:2.

EXAMPLE 2

[1α, 2β, 3α, 5α] 5-cis-2-(t-butyldimethylsilyloxymethyl)-5-hydroxy-3-(tetrahydropyranyloxy)cyclopentane heptenoic acid (3).

To a stirred solution of the (4-carboxybutyl)triphenylphosphonium bromide (15.9 g, 35.9 mmol) in dimethyl sulfoxide (144 mL) at room temperature was added a 1.0M stock solution of sodium bis(trimethylsilyl)amide in tetrahydrofuran (72 mL, 72 mmol) dropwise over about 20 min. The reaction mixture turned slightly yellow then cherry red during this addition. After the addition was complete the reaction was maintained at room temperature for an additional 15 min, then a solution of 2 (8.92 g, 23.9 mmol) in dimethyl sulfoxide (DMSO) (36 mL) was added by canula. After 90 min, the reaction was complete by TLC. The now turbid brown mixture was poured into 350 mL of ice water and neutralized to pH 7 with concentrated HCl (about 25 mL). The reaction was then extracted into ethyl acetate (3×100 mL). The aqueous portion was then acidified to pH 3 with concentrated HCl (about 35 mL) then extracted into additional ethyl acetate (3×100 mL). The combined organic layers were then washed with brine (3×50 mL), dried over anhydrous $MgSO_4$, filtered and concentrated in vacuo to provide acid 3 as a yellow oil.

EXAMPLE 3

[1α, 2β, 3α, 5α] methyl 5-cis-2-(t-butyldimethylsilyl-oxymethyl)- 5-hydroxy-3-tetrahydropyranyloxycyclopentyl) heptenoate (4).

The crude acid 3 was this dissolved in acetone (120 mL) and the reaction flask was placed into a room temperature water bath. The reaction was then added 1,8-diazabicyclo[ 5.4.0] undec-7-ene (DBU) (10.7 mL, 71.8 mmol) followed by iodomethane (MeI) (3.17 mL, 71.8 mmol). The resulting mixture was maintained at room temperature for 14 h, then was poured into ethyl acetate (250 mL) and washed with water (3×50 mL). The combined aqueous washes were then back extracted with ethyl acetate (2×50 mL), then the combined organic layers were washed with water (2×50 mL) and brine ( 2×50 mL). Column chromatography through silica gel (ethyl acetate-hexanes, 1:2) gave 4 (9.18 g, 18.2 mmol, 76%) as a clear, colorless oil. $R_f$=0.42 in ethyl acetatehexanes, 1:4.

EXAMPLE 4

[1α, 2β, 3α, 5α] methyl 5-cis-2-(t-butyldimethyl-silyloxymethyl)- 3,5-di( tetrahydropyranyloxy)cyclopentyl heptenoate (5).

Alcohol 4 was then taken up in dihydopyran (DHP) and toluenesulfonic acid (TsOH) was added. The reaction was maintained at room temperature for 12 h, then was concentrated in vacuo to provide a yellow oil. Column chromatography through silica gel (ethyl acetate-hexanes, 1:2) gave 5 (9.18 g, 18.2 mmol, 76%) as a clear, colorless oil. $R_f$=0.42 in ethyl acetate-hexanes, 1:4.

EXAMPLE 5

[1α, 2β, 3α, 5α] methyl 5-cis-2-hydroxymethyl-3,5di(tetrahydropyranyloxy)cyclopentyl heptenoate (6).

To a solution of 5 (2.14 g, 4.29 mmol) in anhydrous tetrahydrofuran (15 mL) at 0° C. was added dropwise a 1.0M stock solution of tetrabutylammonium fluoride ($Bu_4NF$) in tetrahydrofuran (THF) (6.4 mL, 6.4 mmol) over several seconds. The reaction was allowed to warm slowly to room temperature over 12 h, then was transferred into a separatory funnel with the aid of ethyl acetate (100 mL) and was washed with water (2×20 mL) and brine (2×20 mL). The organic portion was then concentrated in vacuo to a slightly yellow oil (1.71 g, 4.31 mmol, 100%). Column chromatography (50% ethyl acetate in hexanes through 40 mm ID×190 mm L of silica gel) provide 6 (1.65 g, 4.29 mmol, 100%) as a clear, colorless oil. $R_f$=0.27 in ethyl acetate-hexanes, 1:1.

EXAMPLE 6

[1α, 2β, 3α, 5α] methyl 5-cis-2-p-toluenesulfonyloxymethyl-3,5-di(tetrahydropyranyloxy)cyclopentyl heptenoate (7).

To a solution of 6 (1.367 g, 3.10 mmol) in dichloromethane (12.4 mL) at room temperature was added triethylamine ($Et_3$ N) (1.7 mL, 12 mmol), dimethylaminopyridine (DMAP) 36 rag, 0.29 mmol) and toluene sulfonyl chloride (TsCl) (1.77 g, 9.30 mmol). The resulting mixture was maintained at room temperature for 5.5 h, then was diluted with ethyl acetate (70 mL) and washed with water (3×15 mL) and brine (1×15 mL). The organic portion was then concentrated in vacuo to a yellow oil and purified by column chromatography (2:1 hexanes: ethyl acetate) to provide 7 (1.58 g, 2.65 mmol, 86%).

EXAMPLE 7

[1α, 2β, 3α, 5α] methyl 5-cis-3-aminomethyl-3,5di(tetrahydropyranyloxy)cyclopentyl heptenoate (8).

To a solution of 7 (1.24 g, 2.08 mmol) in dimethyl sulfoxide (8 mL) was added sodium azide ($NAN_3$) (650 mg, 10 mmol). The resulting mixture was maintained at heated to 50 ° C. and maintained at that temperature for 12 h. Upon cooling the reaction was diluted with ethyl acetate (40 mL) and washed with water (3×10 mL) then was concentrated in vacuo to provide methyl 3-azidomethyl-3,5di(tetrahydropyranyloxy)cyclopentyl heptenoate. This crude material was dissolved in tetrahydrofuran (10 mL) and to the resulting solution was added triphenyl phosphine (Ph$_3$P) (1.1 g, 4.2 mmol). The resulting mixture was maintained at room temperature for 3 h, then water (110 μL, 6.1 mmol). After an additional 30 min, the reaction was concentrated in vacuo and purified by column chromatography (1:1:10 triethylamine:methanol:ethyl acetate) to provide 8.

EXAMPLE 8a)

[1$_\alpha$, 2$_\beta$, 3$_\alpha$, 5$_\alpha$] methyl
5-cis-2-(methylsulfonamidomethyl)-
3,5-di(tetrahydropyranyloxy)cyclopentyl heptenoate
(9a ).

Figure 1:
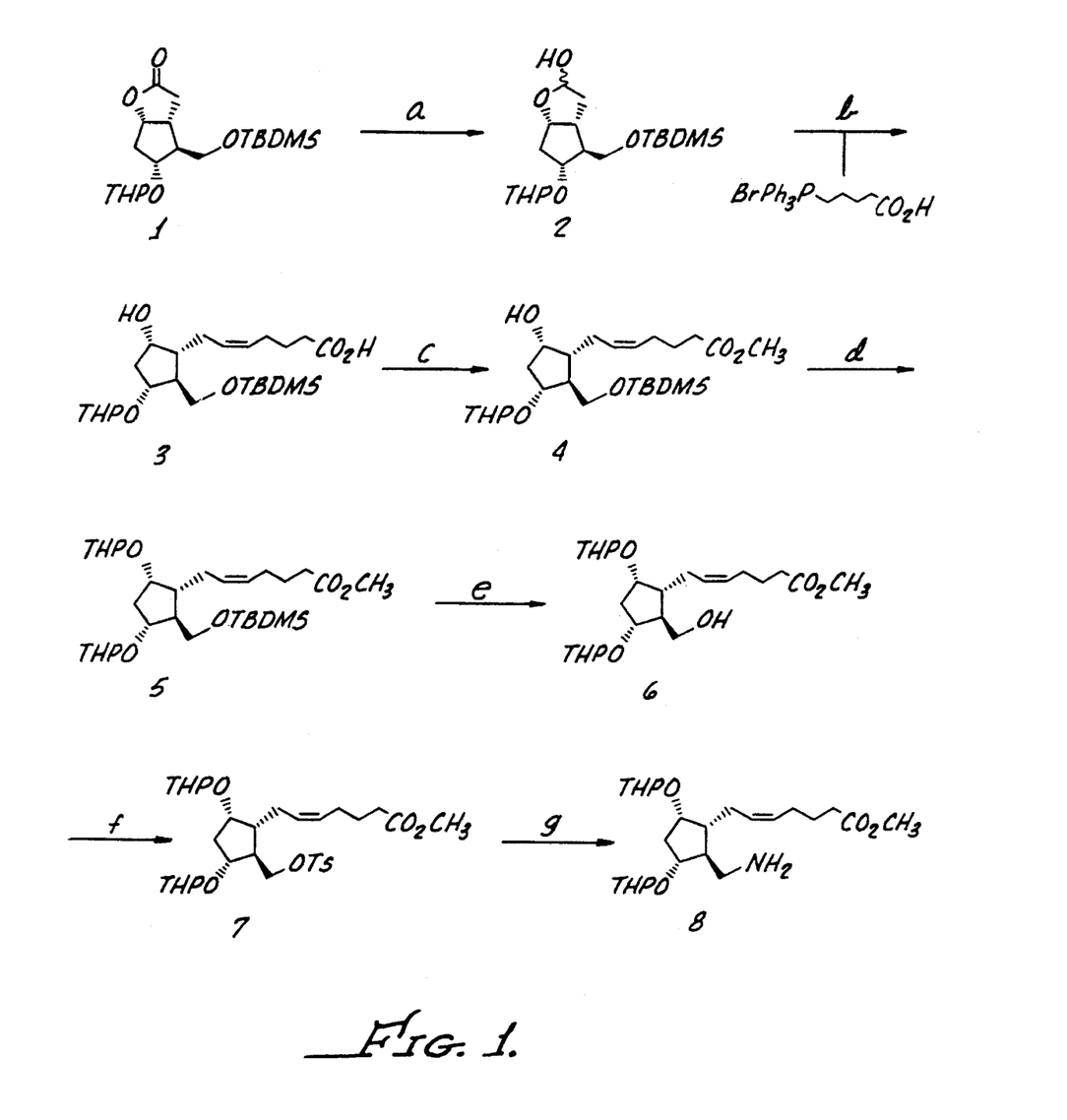
FIG. 1 outlines a general procedure for preparing certain 1-methyl esters of cyclopentane heptenoic acid, 2-aminomethyl which are intermediates in the preparation of certain of the compounds of this invention.
Figure 2:
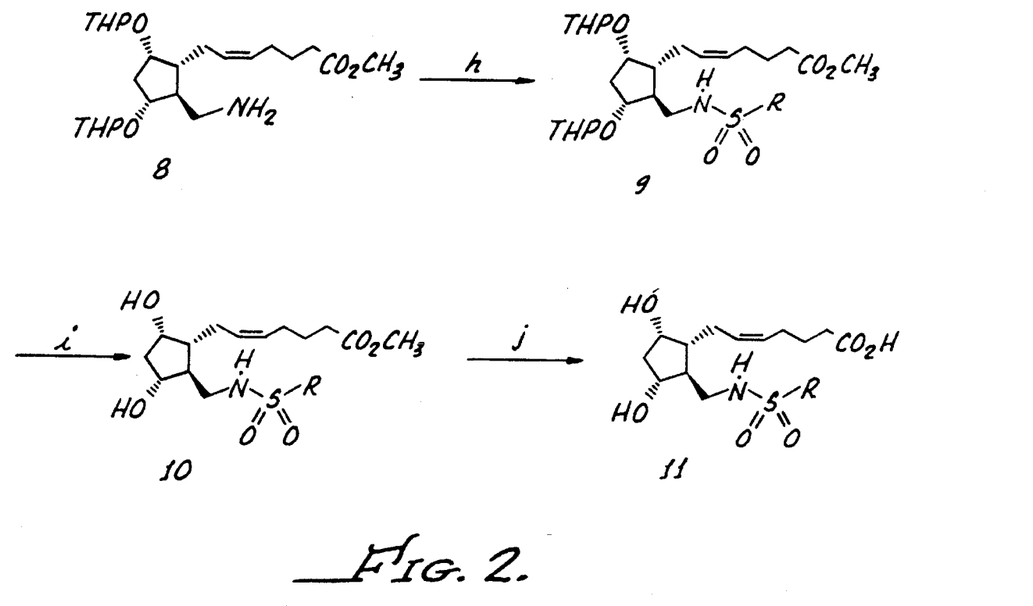
FIG. 2 outlines a general procedure for preparing certain cyclopentane heptenoic acid, 2-hydrocarbylsulfonamidomethyl compounds of the present invention.
Figure 3:
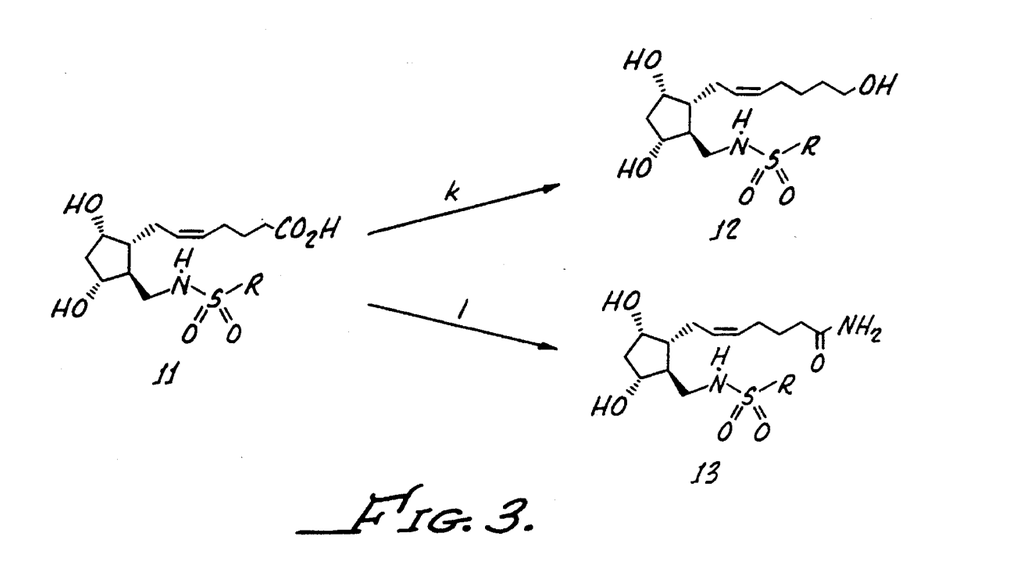
FIG. 3 outlines a general procedure for converting certain cyclopentane heptenoic acid, 2-hydrocarbylsulfonamidomethyl compounds into 1-ol and 1-amido derivatives of the present invention.

To a stirred solution of 8 in dichloromethane (0.9 mL) at room temperature was added triethylamine (18 μL, 0.13 mmol) followed by methanesulfonyl chloride (7.5 μL, 0.097 mmol). (In FIG. 2, R is methyl in this Example.) The resulting solution was maintained a room temperature for 4 h, then was concentrated in vacuo and purified by column chromatography (1:1 hexanes:ethyl acetate) to provide 9a (32.0 mg, 61.8 mmol, 70%).

EXAMPLE 8(b)

[1$_\alpha$, 2$_\beta$, 3$_\alpha$, 5$_\alpha$] methyl
5-cis-2-(n-butylsulfonamidomethyl)-
3,5-di(tetrahydropyranyloxy)cyclopentyl heptenoate
(9b)

Using the general procedure desribed above 8 (41.2 mg, 0.093 mmol) was condensed with n-butanesulfonyl chloride (16.1 mg, 0.103 mmol) to provide 9b. (37.0 mg, 66.1 mmol, 70%). (In FIG. 2, R is n-butyl in this Example.)

EXAMPLE 8(c)

[1$_\alpha$, 2$_\beta$, 3$_\alpha$, 5$_\alpha$] methyl
5-cis-2-(n-pentylsulfonamidomethyl)-
3,5-di(tetrahydropyranyloxy)cyclopentyl heptenoate
(9c).

Using the general procedure desribed above 8 (93.2 mg, 0.212 mmol) was condensed with n-pentanesulfonyl chloride (40 mg, 0.23 mmol) to provide 9c (76.4 mg, 0.133 mmol, 63%). (In FIG. 2, R is n-pentyl in this Example.)

EXAMPLE 8(d)

[1$_\alpha$, 2$_\beta$, 3$_\alpha$, 5$_\alpha$] methyl
5-cis-2-(phenylsulfonamidomethyl)-
3,5-di(tetrahydropyranyloxy)cyclopentyl heptenoate
(9d).

Using the general procedure desribed above 8 (36.6 mg, 0.0832 mmol) was condensed with phenylsulfonyl chloride (16 mg, 0.092 mmol) to provide 9d (29.7 mg, 0.0512 mmol, 61%). (In FIG. 2, R is phenyl in this Example.)

EXAMPLE 8(e)

[1$_\alpha$, 2$_\beta$, 3$_\alpha$, 5$_\alpha$] methyl
5-cis-2-(benzylsulfonamidomethyl)-
3,5-di(tetrahydropyranyloxy)cyclopentyl heptenoate
(9e).

Using the general procedure desribed above 8 (76.2 mg, 0.0173 mmol) was condensed with benzylsulfonyl chloride (36 mg, 0.19 mmol) to provide 9e (54.1 mg, 0.0911 mmol, 53%). (In FIG. 2, R is benzyl in this Example.)

EXAMPLE 8(f)

[1$_\alpha$, 2$_\beta$, 3$_\alpha$, 5$_\alpha$] methyl
5-cis-2-(phenylethylsulfonamidomethyl)-
3,5-di(tetrahydropyranyloxy)cyclopentyl heptenoate
(9f).

Using the general procedure desribed above 8 (111 mg, 0.252 mmol) was condensed with 2-phenylethylsulfonyl chloride (57 mg, 0.28 mmol) to provide 9f (122 mg, 0.201 mmol, 79%). (In FIG. 2, R is phenylethyl in this Example.)

EXAMPLE 8(g)

[1$_\alpha$, 2$_\beta$, 3$_\alpha$, 5$_\alpha$] methyl
5-cis-2-(3phenylpropylsulfonamidomethyl)- 3,5-di(
tetrahydropyranyloxy)cyclopentyl heptenoate (9g).

Using the general procedure desribed above 8 (31.3 mg, 0.0712mmol) was condensed with 3-phenylpropylsulfonyl chloride (17 mg, 0.78 mmol) to provide 9g. (34.0 mg, 0.0547 mmol, 77%). (In FIG. 2, R is phenylpropyl in this Example.)

EXAMPLE 9(a)

[1$_\alpha$, 2$_\beta$, 3$_\alpha$, 5$_\alpha$] methyl
5-cis-2-(methylsulfonamidomethyl)-
3,5-dihydroxycyclopentyl heptenoate (10a).

To a solution of 9a (32.0 mg, 0.0618 mmol) in methanol (1.2 mL) was added p-tohenesulfonic acid monohydrate (6 mg, 0.003 mmol). The resulting mixture was heated to 40° C. and maintained at that temperature for 7 h, thern was concentrated in vacuo. Column chromatography provided 10a (18.2 mg, 0.0521 mmol, 84%).

EXAMPLE 9(b)

[1$_\alpha$, 2$_\beta$, 3$_\alpha$, 5$_\alpha$] methyl
5-cis-2-(n-butylsulfonamidomethyl)-
3,5-dihydroxycyclopentyl heptenoate (10b).

Using the general procedure described above 9b (37.0 mg, 0.0661 mmol) was deprotected to provide 10b (19.9 mg, 0.0508 mmol, 77%).

EXAMPLE 9(c)

[1$_\alpha$, 2$_\beta$, 3$_\alpha$, 5$_\alpha$] methyl
5-cis-2-(n-pentylsulfonamidomethyl)-
3,5-dihydroxycyclopentyl heptenoate (10c).

Using the general procedure described above methyl 9c (76.4 mg, 0.133 mmol) was deprotected to provide 10c (47.1 mg, 0.116 mmol, 87%).

EXAMPLE 9(d)

[1α, 2β, 3α, 5α] methyl 5-cis-2-(phenylsulfonamidomethyl)-3,5-dihydroxycyclopentyl heptenoate (10d).

Using the general procedure described above 9d (29.7 mg, 0.0512 mmol) was deprotected to provide 10d (19.9 mg, 0.0484 mmol, 94 %).

EXAMPLE 9(e)

[1α, 2β, 3α, 5α] methyl 5-cis-2-(benzylsulfonamidomethyl)-3,5-dihydroxycyclopentyl heptenoate (10e).

Using the general procedure described above 9e (54.1 mg, 0.0911 mmol) was deprotected to provide 10e (24.2 mg, 0.0569 mmol, 57%).

EXAMPLE 9(f)

[1α, 2β, 3α, 5α] methyl 5-cis-2-(phenylethylsulfonamidomethyl)-3,5-dihydroxycyclopentyl heptenoate (10f).

Using the general procedure described above 9f (122 mg, 0.201 mmol) was deprotected to provide methyl 10f (69.1 mg, 0.157 mmol, 78%).

EXAMPLE 9(g)

[1α, 2β, 3α, 5α] methyl 5-cis-2-(phenylpropylsulfonamidomethyl)-3,5-dihydroxycyclopentyl heptenoate (10g).

Using the general procedure described above 9 g. (34.0 mg, 0.0547 mmol) was deprotected to provide 10g (18.7 mg, 0.0.0412 mmol, 75%).

EXAMPLE 10(a)

[1α, 2β, 3α, 5α] 5-cis-2-(methylsulfonamidomethyl)-3,5-dihydroxycyclopentyl heptenoic acid (11a).

A solution of 10a (12.7 mg, 0.0349 mmol) in tetrahydrofuran (3 mL) and 0.5 M lithium hydroxide (3 mL) was vigerously stirred at room temperature for 12 h. The resulting mixture was then acidified with concentrated HCl, extracted into chloroform (3×5 mL) and concentrated in vacuo. Column chromatography provided 11a (9.3 mg, 0.027 mmol, 76%). Partial $^1$H NMR (300 MHz) δ 6.5 (m, 4H), 6.2 (bs, 1H), 4.24 (m, 1H), 4.13 (m, 1H), 3.65 (dd, J=7.2, 14.1 Hz, 1H), 3.44 (dd, J=7.0, 14.1 Hz), 3.01 (s, 3H), 2.40 (m, 2H), 1.86 (m, 2H) 1.75-1.20 (m, 9H), 0.96 (m, 1H).

EXAMPLE 10(b)

[1α, 2β, 3α, 5α] 5-cis-2-(n-butylsulfonamidomethyl)-3,5-dihydroxycyclopentyl heptenoic acid (11b).

Using the general procedure described above 10b (21.2 mg, 0.0523 mmol) was saponified to provide 11b (14.0 mg, 0.0358 mmol, 68%). Partial $^1$H NMR (300 MHz) δ 6.7-6.3 (m, 5H), 4.20 (m, 1H), 4.10 (m, 1H), 3.61 (dd, J=7.1, 13.8 Hz, 1H), 3.41 (dd, J=7.0, 13.8 Hz), 3.0 (m, 2H), 2.40 (m, 2H), 1.86 (m, 2H) 1.75-1.20 (m, 15H), 0.89 (m, 1H).

EXAMPLE 10(c)

[1α, 2β, 3α, 5α] 5-cis-2-(n-pentylsulfonamidomethyl)-3,5-dihydroxycyclopentyl heptenoic acid (11c).

Using the general procedure described above 10c (56.4 mg, 0.134 mmol) was deprotected to provide 11c (44.4 mg, 0.109 mmol, 81%). Partial 1H NMR (300 MHz) a 6.7-6.3 (m, 4H), 4.23 (m, 1H), 4.08 (m, 1H), 3.60 (dd, J=7.1, 13.8 Hz, 1H), 3.44 (dd, J=7.0, 13.8 Hz), 3.1 (m, 2H), 2.44 (m, 2H), 1.86 (m, 2H) 1.75-1.15 (m, 14 H), 1.20 (t, J=7.1 Hz, 3H), 0.90 (m, 1H).

EXAMPLE 10(d)

[1α, 2β, 3α, 5α] 5-cis-2-(phenylsulfonamidomethyl)-3,5-dihydroxycyclopentyl heptenoic acid (11d).

Using the general procedure described above 10d (19.3 mg, 0.0453 mmol) was deprotected to provide 11d (12.8 mg, 0.0311 mmol, 68%). Partial $^1$H NMR (300 MHz) δ 6.7-6.3 (m, 5H), 4.20 (m, 1H), 4.10 (m, 1H), 3.61 (dd, J=7.1, 13.8 Hz, 1H), 3.41 (dd, J=7.0, 13.8 Hz), 3.0 (m, 2H), 2.40 (m, 2H), 1.86 (m, 2H) 1.75-1.20 (m, 15H), 0.89 (m, 1H).

EXAMPLE 10(e)

[1α, 2β, 3α, 5α] 5-cis-2-(benzylsulfonamidomethyl)-3,5-dihydroxycyclopentyl heptenoic acid (11e).

Using the general procedure described above 10e (43.5 mg, 0.0435 mmol) was deprotected to provide 11e (17.5 mg, 0.0411 mmol, 41%). Partial $^1$H NMR (300 MHz) δ7.2 (m, 5H), 6.9 (bs, 1H), 6.7-6.3 (m, 4H), 4.20 (m, 1H), 4.10 (m, 1H), 3.80 (m, 4H), 2.40 (m, 2H), 1.86 (m, 2H) 1.75-1.20 (m, 7H), 0.89 (m, 1H).

EXAMPLE 10(f)

[1α, 2β, 3α, 5α] 5-cis-2-(phenylethylsulfonamidomethyl)-3,5-dihydroxycyclopentyl heptenoic acid (11f).

Using the general procedure described above 10f (97.0 mg, 0.213 mmol) was deprotected to provide 2-( 2-phenylethyl)sulfonamidomethyl-3,5-dihydroxycyclopentyl heptenoate 11f (88.2 mg, 0.200 mmol, 94%). Partial $^1$H NMR (300 MHz) δ 7.2 (m, 5H), 6.7-6.4 (m, 5H), 4.27 (m, 1H), 4.11 (m, 1H), 3.8-3.7 (m, 4H), 2.40 (m, 2H), 1.95-1.20 (m, 11H), 0.93 (m, 1H).

EXAMPLE 10(g)

[1α, 2β, 3α, 5α] 5-cis-2-(phenylpropylsulfonamidomethyl)-3,5-dihydroxycyclopentyl heptenoic acid (11g).

Using the general procedure described above 10g .(18.0 mg, 0.0385 mmol) was deprotected to provide 11g (7.3 mg, 0.0161 mmol, 42%). Partial 1H NMR (300 MHz) δ 7.2 (m, 5H), 6.65-6.35 (m, 4H), 6.24 (bs, 1H), 4.18 (m, 1H), 4.05 (m, 1H), 3.8-3.7 (m, 4H), 2.43-2.30 (m, 4H), 1.95-1.20 (m, 13H), 0.88 (m, 1H).

EXAMPLE 11(a) AND 11(b)

[$1_\alpha$, $2_\beta$, $3_\alpha$, $5_\alpha$] 5-cis-2-(methylsulfonamidomethyl)-3,5-dihydroxycyclopentyl hepten-1-ol.

[$1_\alpha$, $2_\beta$, $3_\alpha$, $5_\alpha$]
5-cis-2-(n-butylsulfonamidomethyl)-3,5-dihydroxycyclopentyl hepten-1-ol.

These compounds are prepared by the process of Example 11(c) below, using as starting materials the compounds of Examples 10(a) and 10(b), respectively.

EXAMPLE 11(c)

[$1_\alpha$, $2_\beta$, $3_\alpha$, $5_\alpha$]
5-cis-2-(n-pentylsulfonamidomethyl)-3,5-dihydroxycyclopentyl hepten-1-ol (12c).

To a solution of 10c (21.9 mg, 0.0522 mmol) in tetrahydrofuran at 0° C. was added a 1M stock solution of lithium aluminum hydride (LAH) in tetrahydrofuran. The resulting mixture was maintained at 0° C. for 4 h, then was quenched by addition if acetic acid (1 mL) and concentrated in vacuo. Column chromatorgraphy provided 12c (14.1 mg, 0.0360 mmol, 69%). Partial $^1$H NMR (300 MHz) δ 6.7-6.3 (m, 4H), 4.23 (m, 1H), 4.08 (m, 1H), 3.82 (t, J=7.0 Hz, 2H), 3.66 (dd, J=6.8, 13.8 Hz, 1H), 3.40 (dd, J=6.8, 13.8 Hz), 3.05 (m, 2H), 1.92 (m, 4H) 1.75-1.15 (m, 14H), 1.20 (t, J=7.1 Hz, 3H), 0.90 (m, 1H).

EXAMPLE 11(d) AND 11(e)

[$1_\alpha$, $2_\beta$, $3_\alpha$, $5_\alpha$] 5-cis-2-(phenylsulfonamidomethyl)-3,5dihydroxycyclopentyl hepten-1-ol.

[$1_\alpha$, $2_\beta$, $3_\alpha$, $5_\alpha$] 5-cis-2-(benzylsulfonamidomethyl)-3,5dihydroxycyclopentyl hepten-1-ol.

These compounds are prepared by the process of Example 11(c) below, using as starting materials the compounds of Examples 10(d) and 10(e), respectively.

EXAMPLE 11(f)

[$1_\alpha$, $2_\beta$, $3_\alpha$, $5_\alpha$]
5-cis-2-(phenylethylsulfonamidomethyl)-3,5dihydroxycyclopentyl hepten-1-ol (12f).

Using the general procedure described above 10f (24.4 mg, 0.0521 mmol) was reduced to provide 12f (13.6 mg, 0.0309 mmol, 59%). Partial $^1$H NMR (300 MHz) δ 7.25 (m, 5H), 6.68-6.38 (m, 5H), 4.20 (m, 1H), 4.05 (m, 1H), 3.71 (t, J=6.7 Hz, 2H), 3.63-3.7 (m, 4H), 3.00 (m, 2H), 2.40 (m, 2H), 1.77-1.11 (m, 10H).

EXAMPLE 12(a) AND (b)

[$1_\alpha$, $2_\beta$, $3_\alpha$, $5_\alpha$] 5-cis-2-(methylsulfonamidomethyl)-3,5dihydroxycyclopentyl hepten-1-ol.

[$1_\alpha$, $2_\beta$, $3_\alpha$, $5_\alpha$]
5-cis-2-(n-butylsulfonamidomethyl)-3,5-dihydroxycyclopentyl hepten-1-ol.

These compounds are prepared by the process of Example 12(c) below, using as starting materials the compounds of Examples 10(a) and 10(b), respectively.

EXAMPLE 12(c)

[$1_\alpha$, $2_\beta$, $3_\alpha$, $5_\alpha$]
5-cis-2-(n-pentylsulfonamidomethyl)-3,5-dihydroxycyclopentyl heptenamide (13c).

To a solution of 10c (16.8 mg, 0.00837 mmol) in ammonia was heated in a sealed tube at 50° C. for 12 h. The resulting mixture was then cooled to room temperature and concentrated in vacuo. Column chromatorgraphy provided 3-pentylsulfonamidomethyl- 3,5-dihydroxycyclopentyl heptenamide, 13c, (12.3 mg, 0.0349 mmol, 87%). Partial $^1$H NMR (300 MHz) δ 6.7-6.3 (m, 6H), 4.18 (m, 1H), 4.08 (m, 1H), 3.60 (dd, J=7.1, 13.8 Hz, 1H), 3.44 (dd, J=7.0, 13.8 Hz), 3.1 (m, 2H), 2.14 (m, 2H), 1.86 (m, 2H) 1.75-1.15 (m, 14H), 1.20 (t, J=7.1 Hz, 3H), 0.90 (m, 1H).

EXAMPLE (d) AND (e)

[$1_\alpha$, $2_\beta$, $3_\alpha$, $5_\alpha$] 5-cis-2-(phenylsulfonamidomethyl)-3,5-dihydroxycyclopentyl hepten-1-ol.

[$1_\alpha$, $2_\beta$, $3_\alpha$, $5_\alpha$] 5-cis-2-(benzylsulfonamidomethyl)-3,5dihydroxycyclopentyl hepten-1-ol.

These compounds are prepared by the process of Example 11(c) below, using as starting materials the compounds of Examples 10(d) and 10(e), respectively.

EXAMPLE 12(f)

[$1_\alpha$, $2_\beta$, $3_\alpha$, $5_\alpha$]
5-cis-2-(phenylethylsulfonamidomethyl)-3,5-dihydroxycyclopentyl heptenamide (13f).

Using the general procedure described above 10f (26.4 mg, 0.0582mmol) was reduced to provide 13f (22 mg, 0.050 mmol, 86%). Partial $^1$H NMR (300 MHz) δ 7.2 (m, 5H), 6.7-6.4 (m, 5H), 6.2 (bd, 2H), 4.20 (m, 1H), 4.05 (m, 1H), 3.63-3.7 (m, 4H), 3.00 (m, 2H), 2.40 (m, 2H), 2.10 (t, J=6.8 Hz, 2H), 1.77- 1.11 (m, 10H).

EXAMPLE 13

Intraocular Pressure-Lowering Effects of the Comnounds of the Invention

The effects of certain 2-(alkylsulfonamidomethyl)-3,5-dihydroxycyclopentyl heptenoic acids of the invention on lowering beagle dog intraocular pressure were measured and reported in Table 1, below. Values are mean net changes in mm Hg intraocular pressure. n=6–12: **p<0.01 compared to baseline.

TABLE I

| Compound | Dose | maximum change |
|---|---|---|
| 10f | 0.01% | −2.5** |
| 10f | 0.1% | −5.3** |
| 11f | 0.1% | −2.6** | wherein the numbers in parenthesis refer to the compounds of the Figures.

The foregoing description details specific methods and compositions that can be employed to practice the present invention, and represents the best mode contemplated. However, it is apparent from one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same results. Thus, however detailed the foregoing may appear in text, it should not be construed as limiting the overall scope hereof; rather, the ambit of the present invention is to be governed only by the lawful construction of the appended claims.

I claim:

1. A method of treating ocular hypertension which comprises administering an effective amount of a cyclopentane(ene) heptanoic or cyclopentane(ene) heptenoic acid, 2-hydrocarbylsulfonamidomethyl compound or derivative thereof represented by the formula I wherein the dashed bonds represent a single bond or a double bond which can be in the cis or trans configuration; A is a radical selected from the group consisting of halo, hydrogen, nitro, amino, cyano, azido, thiol and thioether radicals; Z is oxo or represents two hydrogen radicals, provided that Z represents two hydrogen radicals when A is halo, hydrogen, azido, cyano or nitro; B is an alkyl or an alkylcycloalkyl radical having from one to ten carbon atoms, or an arylalkyl radical, selected from the group consisting of hydrocarbyl arylalkyl and heteroarylalkyl radicals wherein the heteroatom is selected from the group consisting of nitrogen, oxygen and sulfur atoms and said arylalkyl radical may comprise up to twelve carbon atoms; $R_3$ is hydrogen or a lower alkyl radical having from 1 to 3 carbon atoms; and one of $R_1$ and $R_2$ is =O, —OH or a —O(CO)$R_6$ group, and the other one is —OH or —O(CO)$R_6$, or $R_1$ is =O and $R_2$ is H, wherein $R_6$ is a saturated or unsaturated acyclic hydrocarbon group having from 1 to about 20 carbon atoms, or —(CH$_2$)$_m$R$_7$ wherein m is 0–10, and $R_7$ is an aliphatic ring from about 3 to about 7 carbon atoms, or an aryl or heteroaryl ring, and pharmaceutically-acceptable salts thereof.

2. The method of claim 1 comprising administering a cyclopentane(ene) heptanoic or cyclopentane(ene) heptenoic acid, 2-(phenyl alkylsulfonamidomethyl) compound represented by the formula II wherein y is 0, or an integer of from 1 to 4, X is a radical selected from the group consisting of halo, nitro, amino, thiol, hydroxy, alkyloxy and alkylcarboxy radicals.

3. The method of treatment of claim 2 wherein said compound is a compound of formula (III).

wherein hatched lines indicate α configuration, and a solid triangle indicates β configuration.

4. The method of claim 3 which comprises administering to a subject a pharmaceutical composition comprising a therapeutically effective amount of a cyclopentane heptenoic acid or derivative thereof of formula (IV)

in combination with a pharmaceutical carrier.

5. The method of claim 4 wherein said compound is selected from compounds of the formula (V)

6. The method of claim 1 wherein B is selected from the group consisting of methyl, ethyl, propyl, butyl, cyclopentylethyl, cyclohexylethyl, phenylethyl, thienylethyl, furanylethyl and pyridylethyl.

7. The method of claim 1 wherein A is selected from the group consisting of —H, —F, —I, —NO$_2$, [—OH,]— N(R$_4$)(R$_4$),—SH and —SR$_5$ [=N—OH, —SH, —SR$_5$ and —OR$_5$] wherein R$_4$ is hydrogen or R$_5$ and R$_5$ is C$_1$ to C$_3$ alkyl.

8. The method of claim 7 wherein A is [—N(R4)(R4)] —N(R$_4$)(R$_4$) [or —OH].

9. The method of claim 8 wherein Z is oxo.

10. The method of claim 7 wherein Z represents 2 hydrogen radicals.

11. A composition useful for treating ocular hypertension Which comprises an effective amount of a cyclopentane(ene) heptanoic or cyclopentane(ene) heptenoic acid, 2hydrocarbylsulfonamidomethyl compound or derivative thereof represented by the formula I wherein the dashed bonds represent a single bond or a double bond which can be in the cis or trans configuration; A is a radical selected from the group consisting of halo, hydrogen, nitro, amino, cyano, azido, thiol and thioether radicals; Z is oxo or represents two hydrogen radicals, provided that Z represents two hydrogen radicals when A is halo, hydrogen, azido, cyano or nitro; B is an alkyl or an alkylcycloalkyl radical having from one to ten carbon atoms, or an arylalkyl radical, selected from the group consisting of hydrocarbyl arylalkyl and heteroarylalkyl radicals wherein the heteroatom is selected from the group consisting of nitrogen, oxygen and sulfur atoms and said arylalkyl radical may comprise up to twelve carbon atoms; $R_3$ is hydrogen or a lower alkyl radical having from 1 to 3 carbon atoms; and one of $R_1$ and $R_2$ is =O, —OH or a —O(CO)$R_6$ group, and the other one is —OH or —O(CO)$R_6$, or $R_1$ is =O and $R_2$ is H, wherein $R_6$ is a saturated or unsaturated acyclic hydrocarbon group having from 1 to about 20 carbon atoms, or —(CH$_2$)$_m$R$_7$ wherein m is 0–10, and $R_7$ is an aliphatic ring from about 3 to about 7 carbon atoms, or an aryl or heteroaryl ring, or a pharmaceutically-acceptable salt thereof, in combination with a pharmaceutically acceptable carrier.

12. The composition of claim 11 comprising administering a cyclopentane(ene) heptanoic or cyclopentane(ene) heptenoic acid, 2-(phenyl alkylsulfonamidomethyl) compound represented by the formula II wherein y is 0, or an integer of from 1 to 4, X is a radical selected from the group consisting of halo, nitro, amino, thiol, hydroxy, alkyloxy and alkylcarboxy radicals.

13. The composition of claim 12 wherein said compound is a compound of formula (III)

wherein hatched lines indicate a configuration, and a solid triangle indicates β configuration.

14. The composition of claim 13 which comprises a therapeutically effective amount of a cyclopentane heptenoic acid or derivative thereof of formula (IV)

15. The composition of claim 14 wherein said compound is selected from compounds of the formula (V)

16. The composition of claim 11 wherein B is selected from the group consisting of methyl, ethyl, propyl, butyl, cyclopentylethyl, cyclohexylethyl, phenylethyl, thienylethyl, furanylethyl and pyridylethyl.

17. The composition of claim 11 wherein A is selected from the group consisting of —H, —F, —I, —NO$_2$, —N(R$_4$)(R$_4$), —SH and —SR$_5$ [=N—OH, —SH, —SR$_5$ and —OR$_5$] wherein $R_4$ is hydrogen or $R_5$ and $R_5$ is $C_1$ to $C_3$ alkyl.

18. The composition of claim 17 wherein A is [—N(R4)(R4)] —N(R$_4$)(R$_4$) [or —OH].

19. The composition of claim 18 wherein Z is oxo.

20. The composition of claim 17 wherein Z represents 2 hydrogen radicals.

21. A compound useful for treating ocular hypertension which comprises a cyclopentane(ene) heptanoic or cyclopentane(ene) heptenoic acid, 2-hydrocarbylsulfonamidomethyl compound or derivative thereof represented by the formula I wherein the dashed bonds represent a single bond or a double bond which can be in the cis or trans configuration; A is a radical selected from the group consisting of halo, hydrogen, nitro, amino, cyano, azido, thiol and thioether radicals; Z is oxo or represents two hydrogen radicals, provided that Z represents two hydrogen radicals when A is halo, hydrogen, azido, cyano or nitro; B is an alkyl or an alkylcycloalkyl radical having from one to ten carbon atoms, or an arylalkyl radical, selected from the group consisting of hydrocarbyl arylalkyl and heteroarylalkyl radicals wherein the heteroatom is selected from the group consisting of nitrogen, oxygen and sulfur atoms and said arylalkyl radical may comprise up to twelve carbon atoms; $R_3$ is hydrogen or a lower alkyl radical having from 1 to 3 carbon atoms; and one of $R_1$ and $R_2$ is =O, —OH or a —O(CO)$R_6$ group, and the other one is —OH or —O(CO)$R_6$, or $R_1$ is =O and $R_2$ is H, wherein $R_6$ is a saturated or unsaturated acyclic hydrocarbon group having from 1 to about 20 carbon atoms, or $—(CH_2)_m R_7$ wherein m is 0–10, and $R_7$ is an aliphatic ring from about 3 to about 7 carbon atoms, or an aryl or heteroaryl ring, and pharmaceutically-acceptable salts thereof.

22. The compound of claim 21 comprising a cyclopentane(ene) heptanoic or cyclopentane(ene) heptenoic acid, 2-(phenyl alkylsulfonamidomethyl) compound represented by the formula II wherein y is 0, or an integer of from 1 to 4, X is a radical selected from the group consisting of halo, nitro, amino, thiol, hydroxy, alkyloxy and alkylcarboxy radicals.

23. The compound of claim 22 wherein said compound is a compound of formula (III).

wherein hatched lines indicate α configuration, and a solid triangle indicates β configuration.

24. The compound of claim 23 comprising a therapeutically effective amount of a cyclopentane heptenoic acid or derivative thereof of formula (IV)

25. The compound of claim 24 wherein said compound is selected from compounds of the formula (V)

26. The compound of claim 21 wherein B is selected from the group consisting of methyl, ethyl, propyl, butyl, cyclopentylethyl, cyclohexylethyl, phenylethyl, thienylethyl, furanylethyl and pyridylethyl.

27. The compound of claim 21 wherein A is selected from the group consisting of —H, —F, —I, —NO$_2$, —N($R_4$)($R_4$), —SH and —SR$_5$ [=N—OH, —SH, —SH$_5$ and —OR$_5$] wherein $R_4$ is hydrogen or $R_5$ and $R_5$ is $C_1$ to $C_3$ alkyl.

28. The compound of claim 7 wherein A is [—N(R4)(R4)] —N($R_4$)($R_4$)[or —OH].

29. The compound of claim 8 wherein Z is oxo.

30. The compound of claim 7 wherein Z represents 2 hydrogen radicals.

* * * * *